(12) United States Patent
Tedesco (10) Patent No.: US 10,481,385 B2
(45) Date of Patent: Nov. 19, 2019

(54) ENDOSCOPIC IMMERSION PROBE END OPTICS FOR LASER SPECTROSCOPY

(71) Applicant: Kaiser Optical Systems Inc., Ann Arbor, MI (US)

(72) Inventor: James M. Tedesco, Livonia, MI (US)

(73) Assignee: Kaiser Optical Systems Inc., Ann Arbor, MI (US)

( * ) Notice: Subject to any disclaimer, the term of this patent is extended or adjusted under 35 U.S.C. 154(b) by 0 days.

(21) Appl. No.: 15/592,506

(22) Filed: May 11, 2017

(65) Prior Publication Data

US 2018/0329196 A1    Nov. 15, 2018

(51) Int. Cl.
| | |
|---|---|
| *G02B 23/24* | (2006.01) |
| *G01J 3/44* | (2006.01) |
| *G01N 21/64* | (2006.01) |
| *G01N 21/65* | (2006.01) |
| *G01N 21/85* | (2006.01) |
| *G01J 3/02* | (2006.01) |
| *A61B 1/00* | (2006.01) |

(52) U.S. Cl.
CPC .......... *G02B 23/243* (2013.01); *G01J 3/0208* (2013.01); *G01J 3/0218* (2013.01); *G01J 3/44* (2013.01); *G01N 21/645* (2013.01); *G01N 21/65* (2013.01); *G01N 21/8507* (2013.01); *G02B 23/2446* (2013.01); *G02B 23/2469* (2013.01); *A61B 1/00064* (2013.01)

(58) Field of Classification Search
CPC . G02B 7/00; G02B 7/003; G02B 7/02; G02B 7/021; G02B 7/04; G02B 13/0095; G02B 13/16; G02B 23/00; G02B 23/14; G02B 23/16; G02B 23/24; G02B 23/2407; G02B 23/2423; G02B 23/243; G02B 23/2446; G02B 23/2453; G02B 23/2461; G02B 23/2469; G02B 23/2476; G02B 23/26
See application file for complete search history.

(56) References Cited

U.S. PATENT DOCUMENTS

| | | | | |
|---|---|---|---|---|
| 3,959,581 | A * | 5/1976 | Laub .................... | G02B 13/22 369/112.24 |
| 5,309,541 | A * | 5/1994 | Flint ..................... | G02B 6/102 359/365 |
| 6,907,149 | B2 * | 6/2005 | Slater ................... | G01N 21/645 250/227.11 |
| 2004/0245445 | A1 * | 12/2004 | Suzuki ................. | G01N 21/6458 250/234 |

(Continued)

*Primary Examiner* — Thong Q Nguyen
(74) *Attorney, Agent, or Firm* — Christopher R. Powers; PatServe (57) ABSTRACT

In one aspect of the present disclosure, improved end optics are disclosed that maximize the numerical aperture focused at a sample point while minimizing unwanted artifacts such as vignetting. The configurations also maintain centering of the excitation/collection beam on the objective if the probe tilts or bends. The disclosed configurations are particularly suited to probes wherein the excitation and/or collection paths between the probe and the laser/analyzer are coupled through multimode fibers, such as in Raman and other forms of laser spectroscopy. The disclosure includes the insertion of one or more additional lenses between the probe head and the focusing objective at the probe tip.

10 Claims, 10 Drawing Sheets

(56) References Cited

U.S. PATENT DOCUMENTS

| | | | | |
|---|---|---|---|---|
| 2007/0057211 A1* | 3/2007 | Bahlman | ............ | G01N 21/6452 |
| | | | | 250/584 |
| 2009/0152440 A1* | 6/2009 | Altendorf | .......... | G01B 11/0608 |
| | | | | 250/201.4 |
| 2010/0002560 A1* | 1/2010 | Yamasaki | ............ | G11B 7/1376 |
| | | | | 369/112.23 |
| 2012/0026462 A1* | 2/2012 | Uhlhorn | ................. | A61B 3/102 |
| | | | | 351/206 |
| 2016/0178439 A1* | 6/2016 | Freudiger | ................. | G01J 3/44 |
| | | | | 356/301 |
| 2016/0345820 A1* | 12/2016 | Frisken | ................ | A61B 3/0025 |

* cited by examiner (PRIOR ART)

ENDOSCOPIC IMMERSION PROBE END OPTICS FOR LASER SPECTROSCOPY

TECHNICAL FIELD

The present disclosure relates generally to laser spectroscopy and, in particular, to immersive end optics.

BACKGROUND

For in situ Raman monitoring and other applications, there is a need to couple elongated end optics to probe heads used to deliver laser excitation and collect sample spectra. However, quality issues arise with longer probe lengths. In particular, it is difficult to maintain alignment of the beam path from the probe head through long, thin immersion end optics. Tolerances on straightness and stiffness of the optic tube are difficult to maintain, resulting of vignetting of the beam at the focusing objective at the distal end of the probe, especially under mechanical stress. Such problems are further exacerbated by the beam divergence inherent in Raman probe heads that are coupled to an analyzer via large-core multimode optical fibers.

Figure 1:
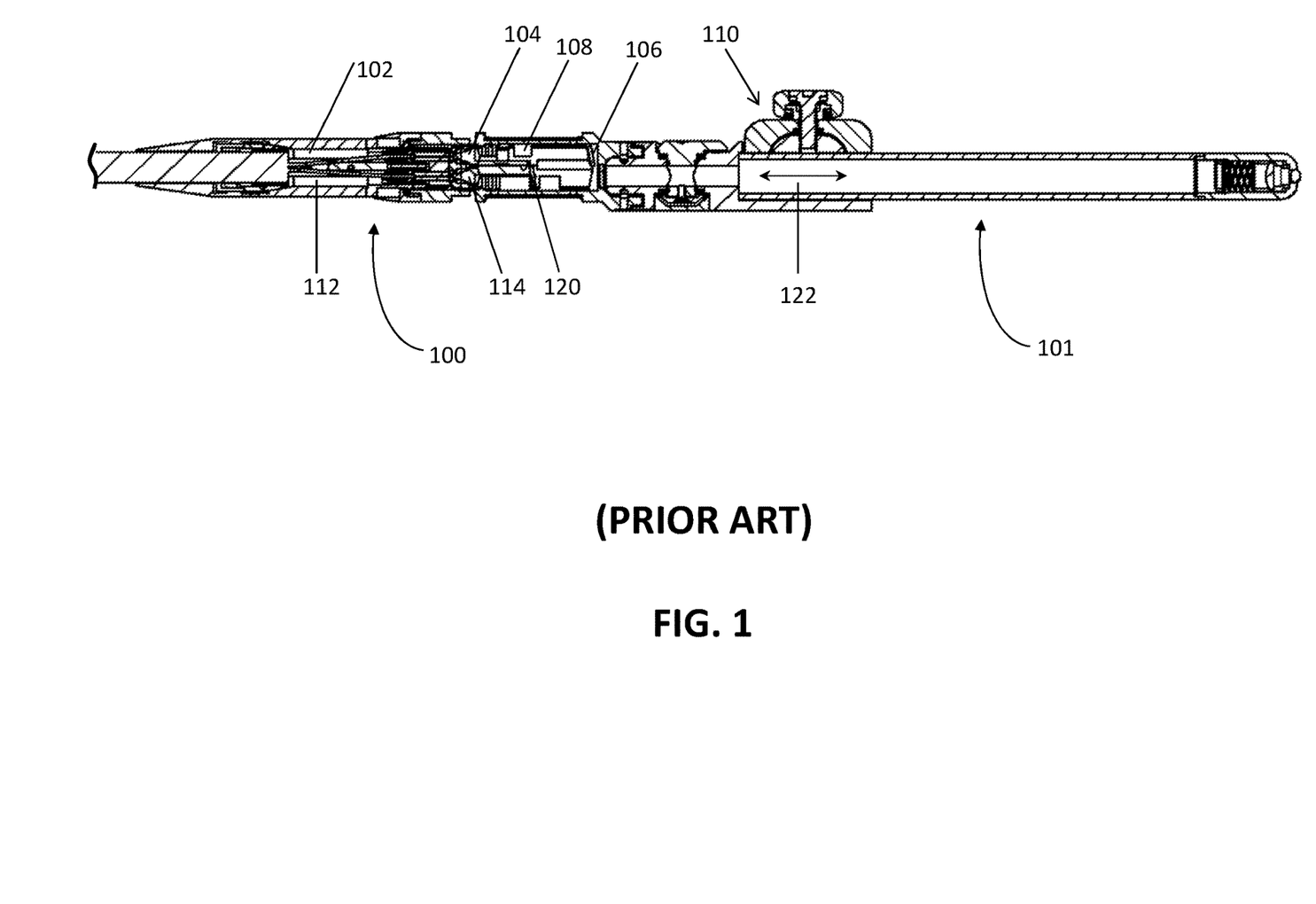
FIG. 1 is a cross sectional diagram of a prior-art fiber-coupled Raman probe head.

FIG. 1 is a cross sectional diagram of an MR-type filtered fiber-coupled Raman probe head 100 available from Kaiser Optical Systems, Inc. of Ann Arbor, Mich. The probe head 100 interfaces via collet 110 to end optic tube 101. Different end optics are available in various lengths and focal depths for different applications including in situ insertion/immersion Raman analysis of reaction vessels, automated laboratory reactors, extruders, process streams, and so forth.

As described in U.S. Pat. No. 6,907,149, incorporated herein by reference, laser excitation is brought into the probe head 100 via fiber 102, which is then collimated by lens 104. The collimated light then passes through a bandpass filter 108 to remove non-laser wavelengths generated en route from the source. The filtered light is reflected by a mirror 106 onto a beam combiner 120 which then enters the end optic tube 101 as a counter-propagating beam 122. The light scattered by the sample beyond the distal end of end optic tube 101 returns along the same counter-propagating beam path 122, passes through beam combiner 120 in the reverse direction, and is filtered by an optional notch filter (not shown) before being focused by lens 114 onto the end of collection fiber 112.

Figure 2:
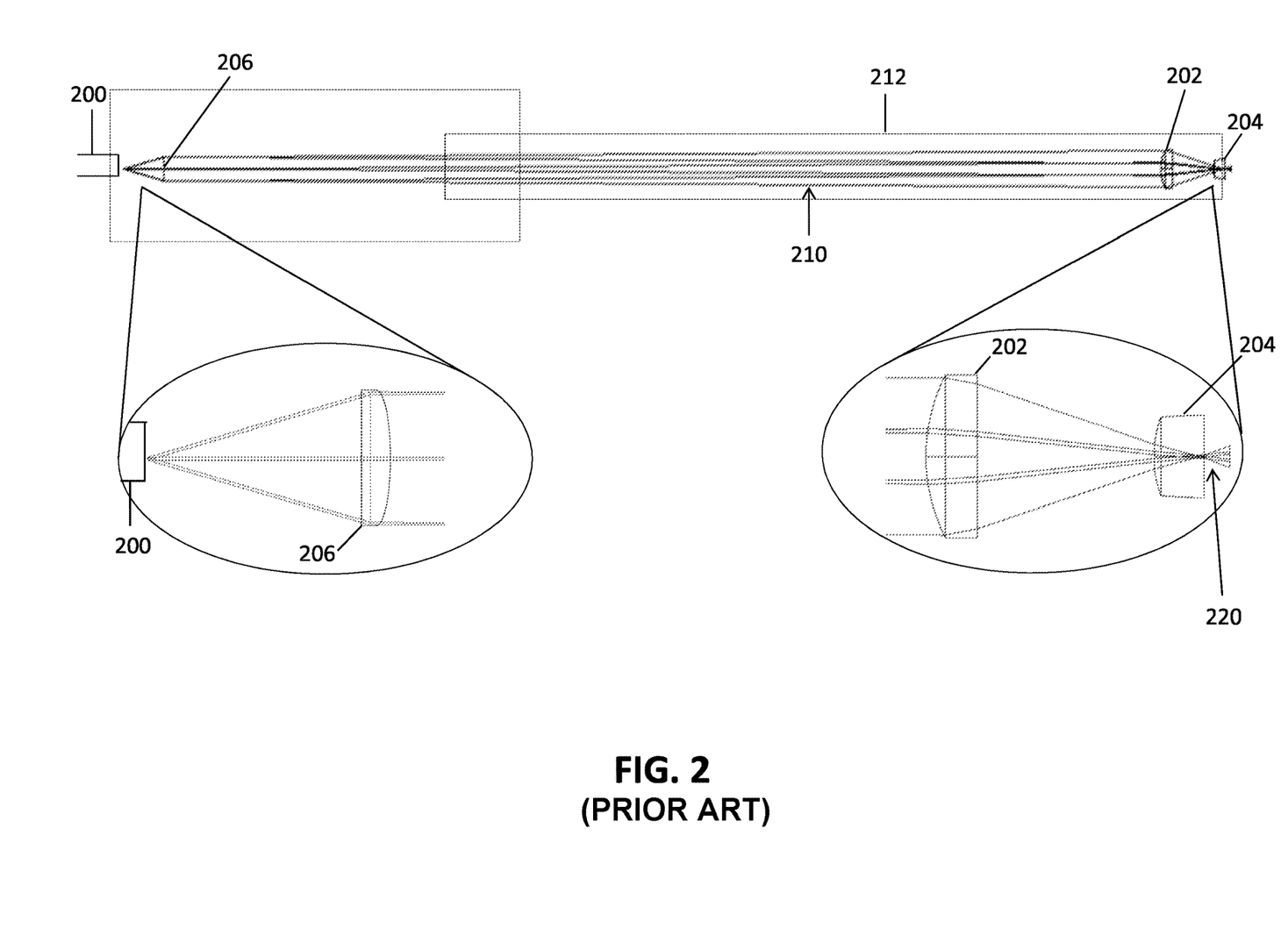
FIG. 2 is a simplified illustration of the probe head of FIG. 1 including an end optic for immersive sample analysis.

FIG. 2 is a simplified diagram of the probe head end optic of FIG. 1. Due to the beam distribution and filtering functions in the probe head, the probe head is typically larger than an allowable sample interface, which may require tubes of varying lengths and/or sizes for immersion in various sample vessels. Note that while "tubes" are used with reference to sealed immersion optics, the concept can be generalized to any suitable support structure for the optics. Input optical fiber 200 has a high numerical aperture (NA) at the edges of the fiber core, which is focused at infinity by collimating lens 206, establishing the excitation-collection beam 210 within the tube 212 of the end optic. The distal end of the optic includes a focus lens 202 and window lens objective assembly 204, which together form an image of the fiber at a focal point 220 just outside the window 204 within the sample (i.e., sample focus 220).

Figure 3:
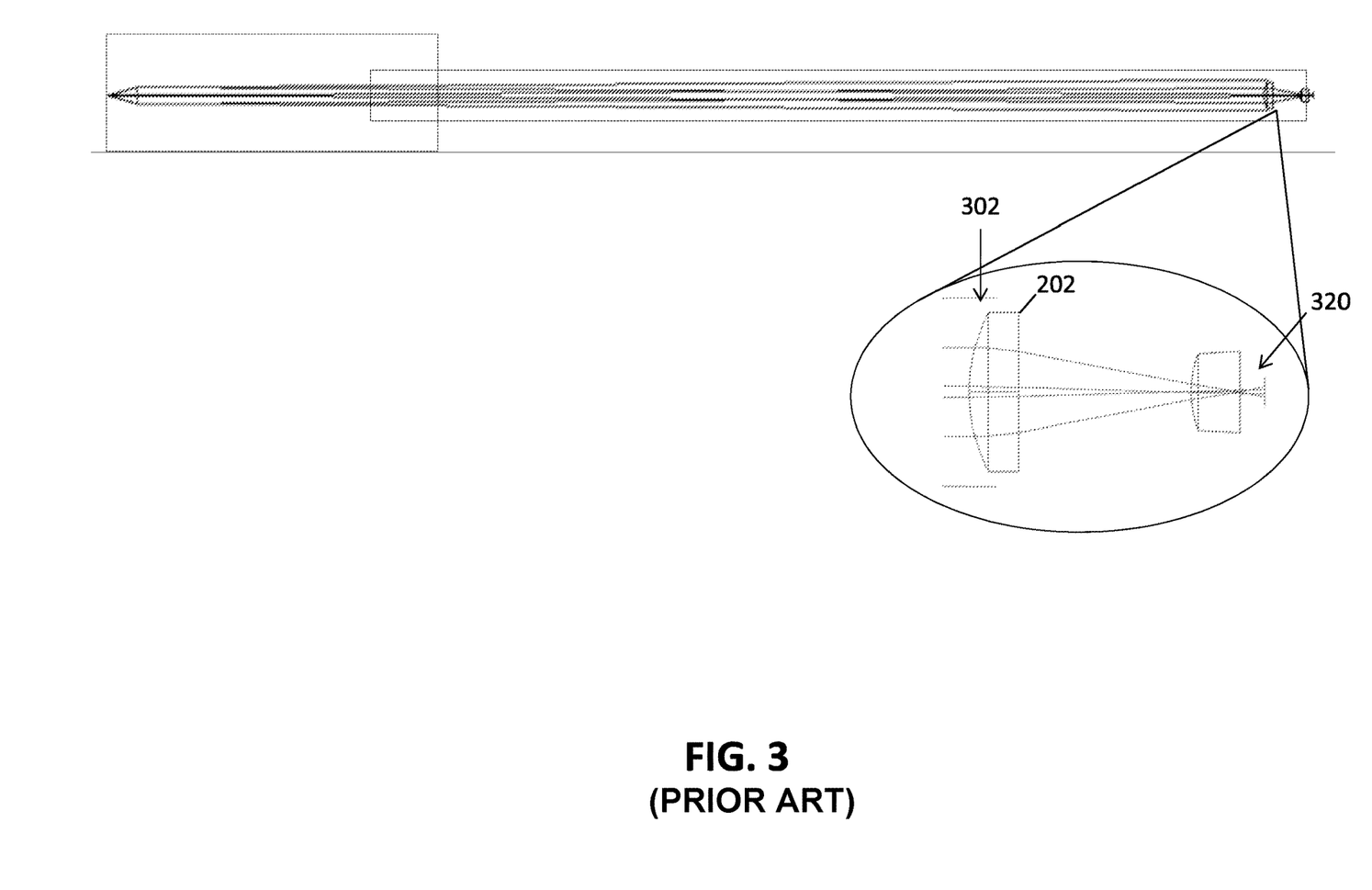
FIG. 3 illustrates divergence of a beam within a tube with longer end optics causing the optical path from the probe head to "overfill" the focus lens, resulting in less efficient focusing at point within the sample.

The divergence of the beam within the probe tube 212 is determined by the diameter of the fiber core 200 and the focal length of collimating lens 206. With shorter tubes, the beam size expansion due to divergence is limited, and the entire beam path is transmitted efficiently into the sample at focus 220. However, some applications require longer tubes, including tubes with lengths of 500 mm or more. At such lengths, as depicted in FIG. 3, divergence of the beam at 302 causes the optical path from the probe head to "overfill" focus lens 202, which in turn results in the beam path being blocked with less efficient focusing or vignetting at sample focus 320 within the sample.

The need remains, therefore, for a solution to the problem of vignetting in elongated end optics for in situ spectroscopic probes.

SUMMARY

The present disclosure is directed to end optics adapted for use with a spectroscopic probe head including an input fiber directed to a collimating lens having an aperture for collimating and focusing a counter-propagating excitation and collection beam. Such probe heads are common in Raman spectroscopy and other fields such as fluorescence. In addition to the minimization of unwanted optical artifacts such as vignetting, the end optic of the present disclosure maintains centering of the beam centered on the objective as the probe tilts or bends. The configurations disclosed herein are particularly suited to probes wherein the excitation and/or collection paths between the probe and the laser/analyzer are coupled through multimode fibers.

The disclosed solutions involve the insertion of one or more additional lenses between the probe head and the focusing objective at the probe tip. While a hollow tube with a distal, sealed window may be used for immersive end optics, any support structure serving as an 'optical bench' may be used to position and maintain the various optical components in optical alignment.

The proximal end of the optical support structure interfaces to a probe head such that the support structure carries a counter-propagating excitation-collection beam to and from the sample. A window or other form of optical interface is disposed at the distal end of the support structure. The system includes a focusing objective having an aperture for focusing the beam at a focus point in a sample immediately adjacent to the optical interface. In accordance with the present disclosure, at least one intermediate lens is provided to reduce overfilling of the focusing objective aperture with the beam and reduce vignetting.

The intermediate lens may be a first intermediate lens, disposed at the proximal end of the support structure, with a focal length selected to generate an image of the input fiber at the focusing objective. A second intermediate lens may be disposed between the first intermediate lens and the focusing objective. In such an embodiment, the first intermediate lens forms an image of the input fiber at or near the second intermediate lens, while the second intermediate lens is operative to relay the collimating lens aperture to an image at or near the focus lens, and steer the beam toward the center of the focusing objective in response to a bending of the optical support structure.

The second intermediate lens may be operative to generate an image of the collimating lens aperture at a point beyond the focusing objective to increase beam filling of the focusing objective aperture and improve the numerical aperture at the focus point in the sample. In all embodiments, the second intermediate lens may be positioned in a region approximately midway along the length of the support structure.

The first intermediate lens may have a focal length selected to generate an image of the fiber at a point beyond the focusing objective to increase beam filling of the focusing objective aperture and improve the numerical aperture at the focus point in the sample. A second intermediate lens, disposed between the first intermediate lens and the focusing objective, may be provided to steer the beam toward the center of the focusing objective in response to a bending of the optical support structure.

DETAILED DESCRIPTION

The present disclosure addresses problems associated with vignetting in elongated end optics for in situ probes such as Raman probes, though the disclosed solutions are applicable to other measurement techniques including fluorescence. The configurations disclosed herein are particularly suited to probes wherein the excitation and/or collection paths between the probe and the laser/analyzer are coupled through multimode fibers. In broad and general terms, the solution involves the insertion of one or more additional lenses between the probe head and the focusing objective at the probe tip. In addition to the minimization of unwanted optical artifacts such as vignetting, the configurations of the present disclosure described herein maintain centering of the beam centered on the objective as the probe tilts or bends.

As described in the various embodiments disclosed here, such additional lenses may be incorporated into the barrel or tube of the end optic itself. However, while a hollow tube with a distal, sealed window is a logical choice for immersive end optics, the present disclosure is not limited in this regard. In particular, any support structure serving as an 'optical bench' may be used to position and maintain the various optical components in optical alignment. In addition to a distal window, direct sample exposure and/or the use of sample vessels such as cuvettes may alternatively be used.

The approach is partially analogous to the intermediate or "relay" lenses used in medical imaging endoscopes, but with far fewer constraints. In conventional imaging endoscopes, the goal generally is to generate a two-dimensional visual image with reasonably high spatial resolution. In the case of the present disclosure, however, the objective is to concentrate the energy in a laser excitation beam (and coaxial collection path for laser-excited emissions from the illuminated sample) to a region in close proximity to the distal window of the probe, with minimal or no vignetting. This difference in objectives leads to different requirements and, thus, structures for solutions.

In accordance with the present disclosure, it is not required that the concentrated energy region in the sample corresponds to an image of the fiber at the probe head, as is conventional practice. Indeed, comparable performance is obtained regardless of whether the probe "focus" corresponds to either an image of the probe head fiber or alternatively an image of a lens aperture in the probe head, such as the fiber collimator aperture. This enables relatively simple, low cost optics in comparison to conventional endoscope designs.

In the embodiments of the present disclosure described herein, three rays are shown, traced from each of two different edges of a multimode input fiber. For the purposes of illustration/clarification, fiber images are then seen as rays converging to two points at an axial location, whereas lens aperture images converge to three points at an axial location.

Figure 4:
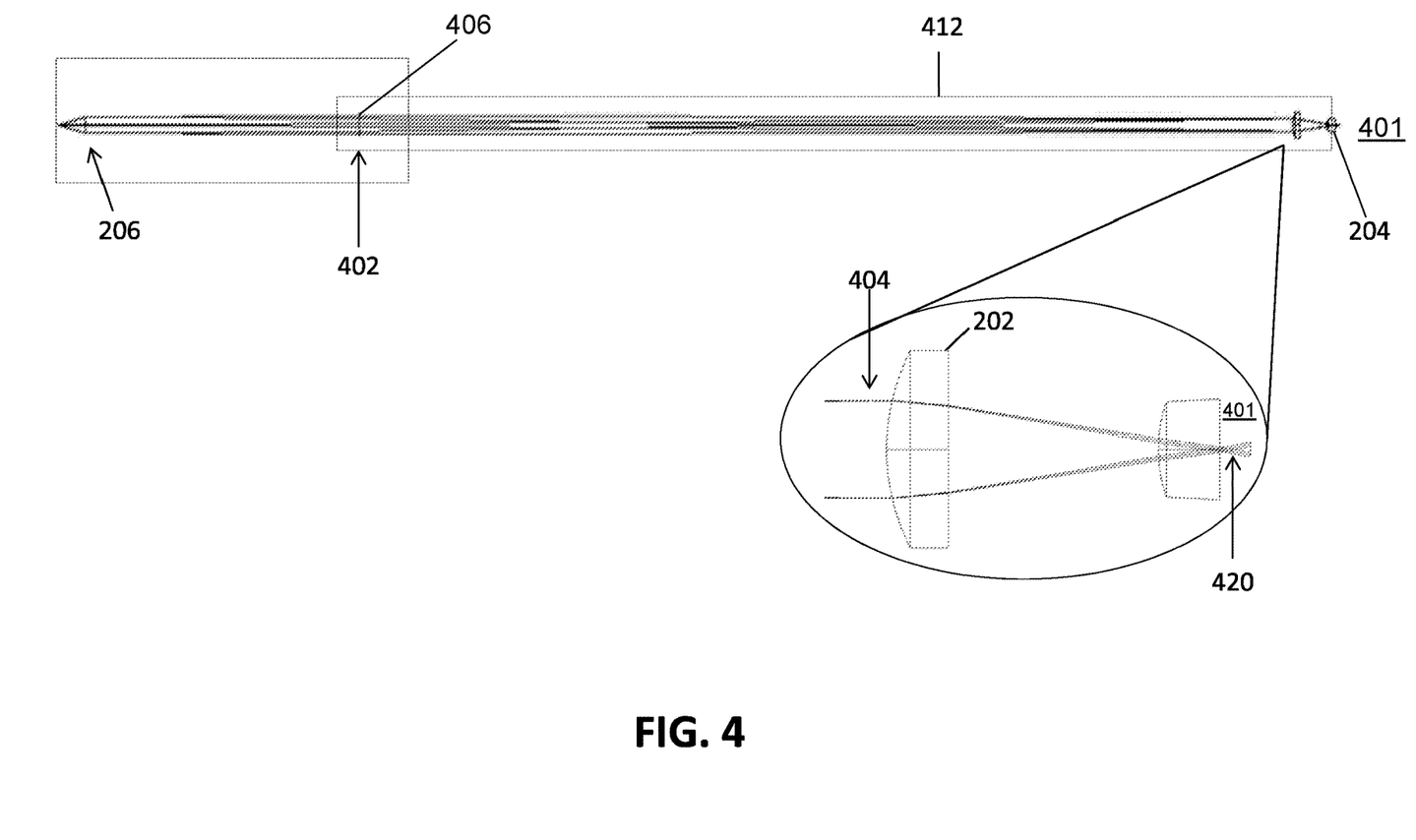
FIG. 4 depicts an embodiment according to the present disclosure.

FIG. 4 illustrates an embodiment of the present disclosure. In this case, an intermediate lens 406 is positioned at a point 402, at or near the proximal input end of an end optic tube 412. The intermediate lens 406 essentially "compresses" a diverging collimated image of an extended source multimode input fiber provided by lens 206, reducing the spread of the beam within the tube, forming an image of the input fiber 404 to be formed nominally at focus lens 202 at the distal end of the probe. The beam does not overfill (as illustrated in FIG. 3) the focus lens 202, and the focus within a sample 401 at sample focus 420 is now an image of the probe head lens aperture and not the fiber.

Figure 5:
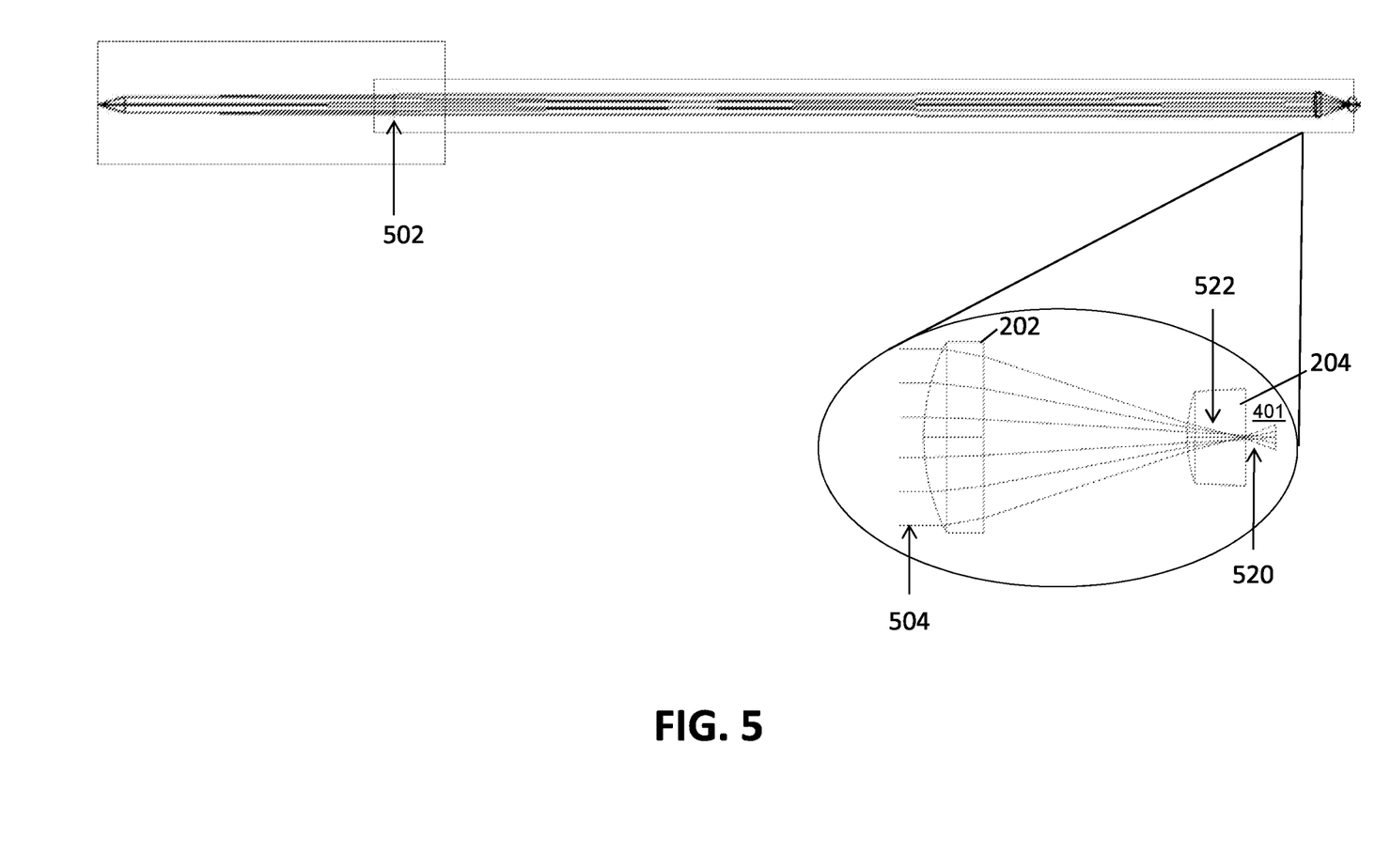
FIG. 5 shows a further embodiment wherein a longer focal length lens is selected to "compress" the beam so as to better fill the objective aperture of the focusing lens.

While the arrangement of FIG. 4 improves laser beam transmission on the excitation path for longer end optic assemblies, the solution as pictured for the tube length of FIG. 4 is sub-optimal insofar as the fiber image formed at the focus lens significantly underfills the focus lens 202. Underfilling the focus lens 202 results in reduced numerical aperture on the sample collection path, in turn reducing the solid angle of the omnidirectional light scatter collected from the sample. An improved solution for such a configuration is depicted in FIG. 5, in which a longer focal length lens 502 is selected to "compress" the beam a bit less than in the embodiment of FIG. 4 so as to better fill the objective aperture of the focus lens 202. The focus lens 202 is now neither overfilled nor underfilled at point 504, thereby recovering the numerical aperture at the sample for improved light collection. Again, however, the sample focus 520 in the sample 401 is still an image of the probe head lens aperture and not the fiber. Indeed, the fiber image is now positioned beyond the focus lens 202 and is within the window 204 at a position 522 in this example.

Figure 6:
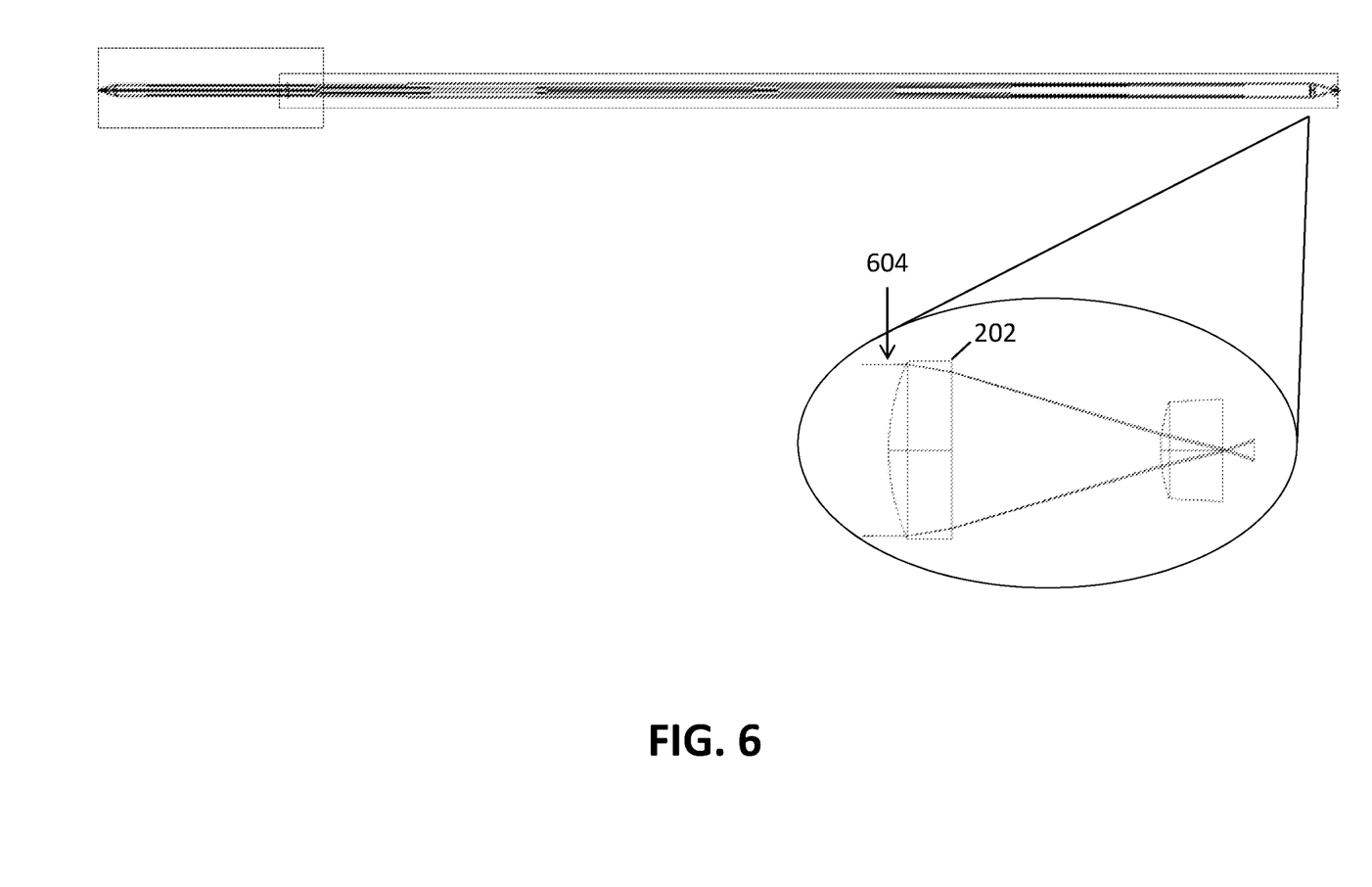
FIG. 6 illustrates how longer end optics may require a longer focal length intermediate lens, which in turn generates a larger fiber image (i.e., minimum beam footprint) at the focus lens.

Even with the above-described solutions, at extended lengths, the fiber image may become too large, and may again overfill the objective of the focus lens 202. As shown in FIG. 6, longer end optics require a longer focal length intermediate lens, which in turn generates a larger fiber image 604 (minimum beam footprint) at focus lens 202. With such a condition, it can be seen that any additional tube length will overfill focus lens. To address this problem, additional intermediate lenses may be incorporated into the tube of the end optic.

Figure 7:
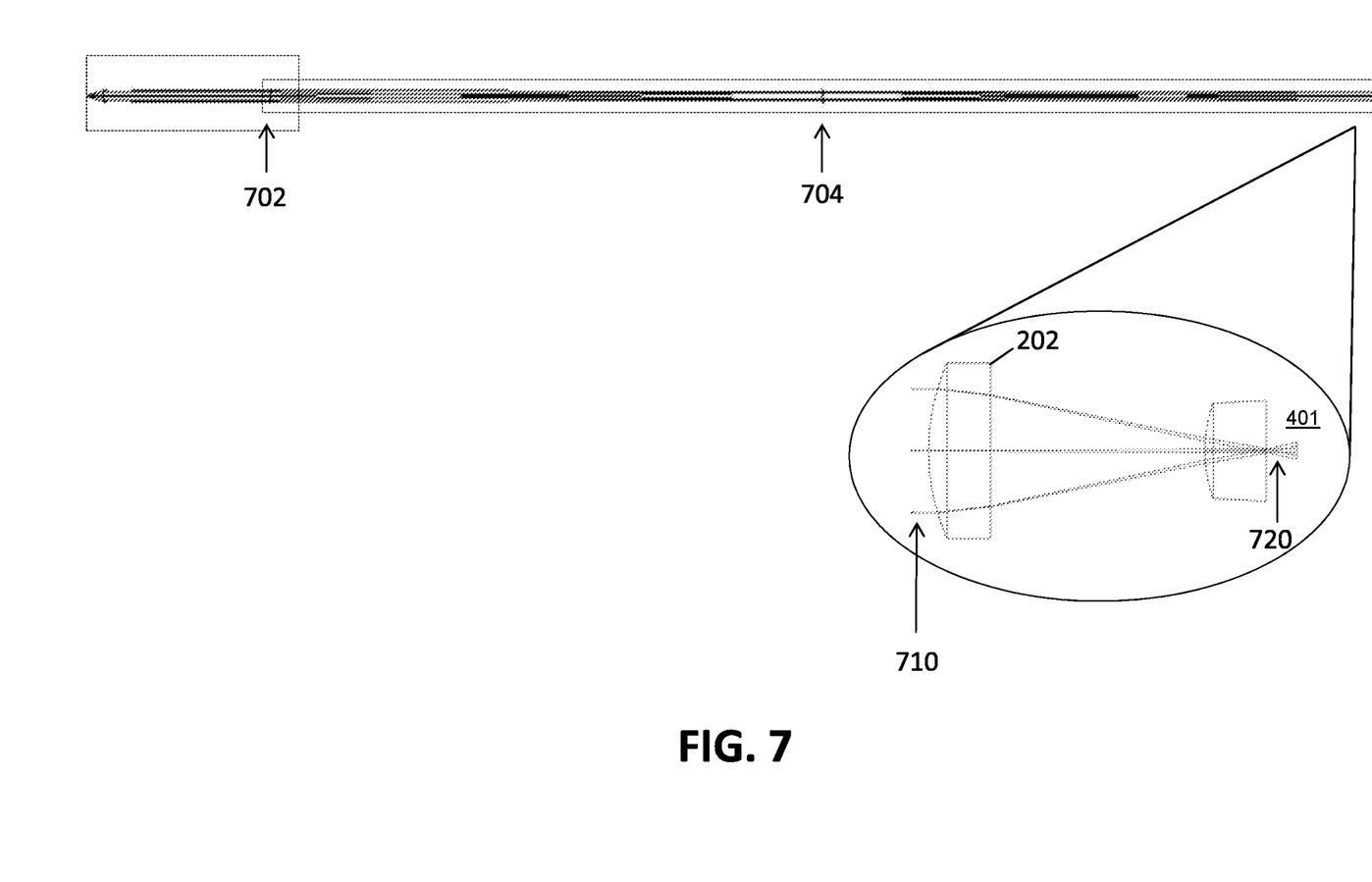
FIG. 7 illustrates that for end optics longer than a proximal intermediate lens design allows, a second intermediate lens may be added to relay the probe lens aperture to focus lens.

As shown in FIG. 7, for end optics longer than a proximal intermediate lens design allows, a second intermediate lens 704 (i.e., a field lens) may be added to (nominally) relay the first intermediate lens aperture to the focus lens 202. Positioned approximately half way along the length of the tube, the second intermediate lens 704 "desensitizes" the long end optic to vignetting due to mechanical bending or angular error at the collet interface. The aperture of focus lens 202 is now underfilled at point 710, and the sample focus 720 in the sample 401 is now a relayed image of the fiber and not an image of the probe lens aperture.

Figure 8:
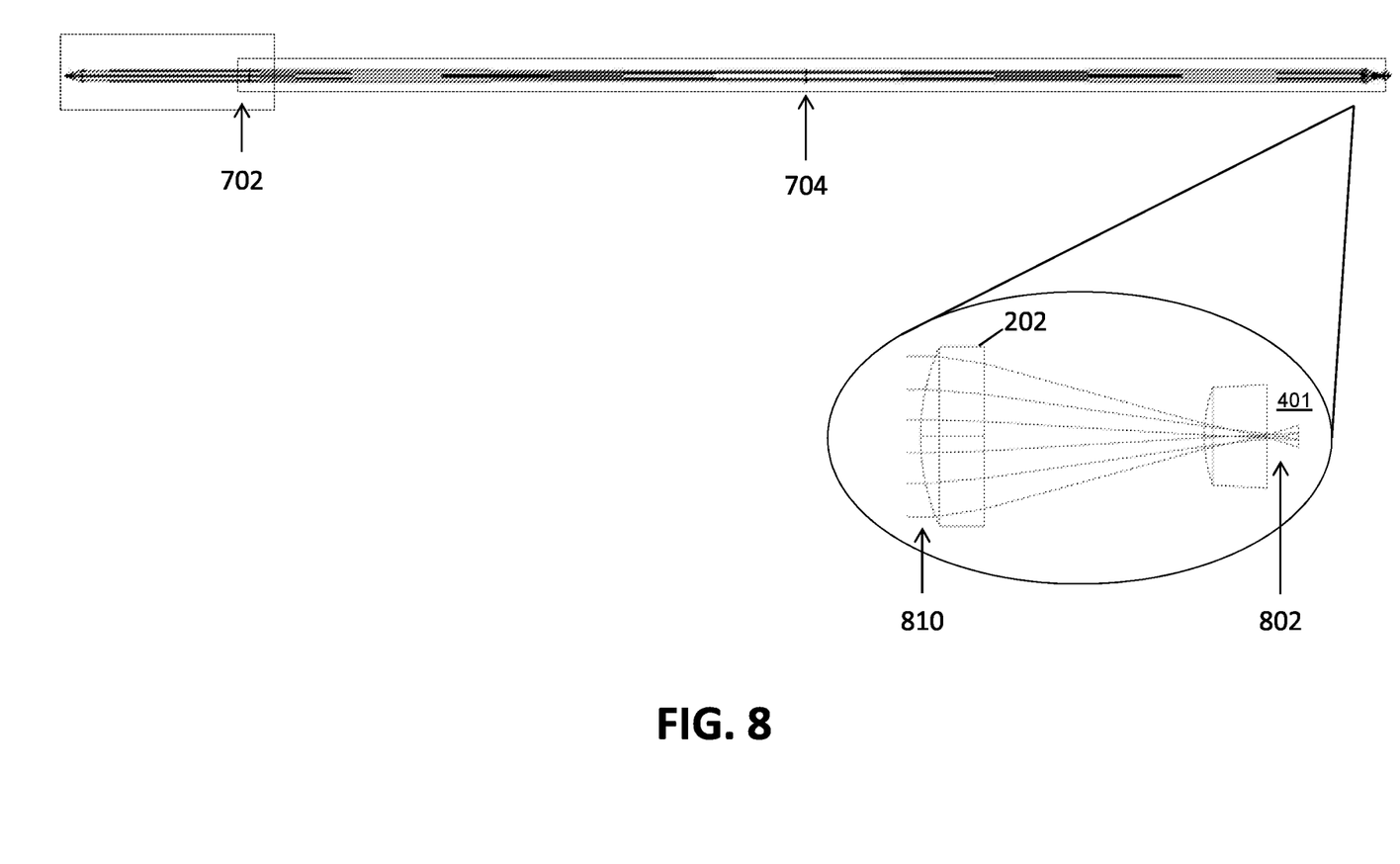
FIG. 8 shows the how a longer focal length at the second intermediate lens better fills the focus lens.

If the focus lens is underfilled by imaging the probe aperture to the focus lens with the second intermediate lens 704, the focal length can be further modified to better fill the focus lens 202 for an improved numerical aperture at the sample. As shown in FIG. 8, the focal length of first intermediate lens 702 may be selected to image the fiber at (or near) a second intermediate lens 704. The longer focal length of lens 704 images the probe lens aperture beyond the focus lens 202 to better fill the focus lens aperture. The focus lens 202 is neither overfilled nor underfilled at point 810, and the sample focus 802 in the sample 401 is now a relayed image of the fiber.

Although a wide coverage of the focus lens is desirable for an improved numerical aperture at the sample, design tradeoffs do exist. For example, it may be desirable to underfill longer tubes more than shorter tubes because of potential flexing of the tube, which could otherwise move the focus lens out of the beam path.

Figure 9:
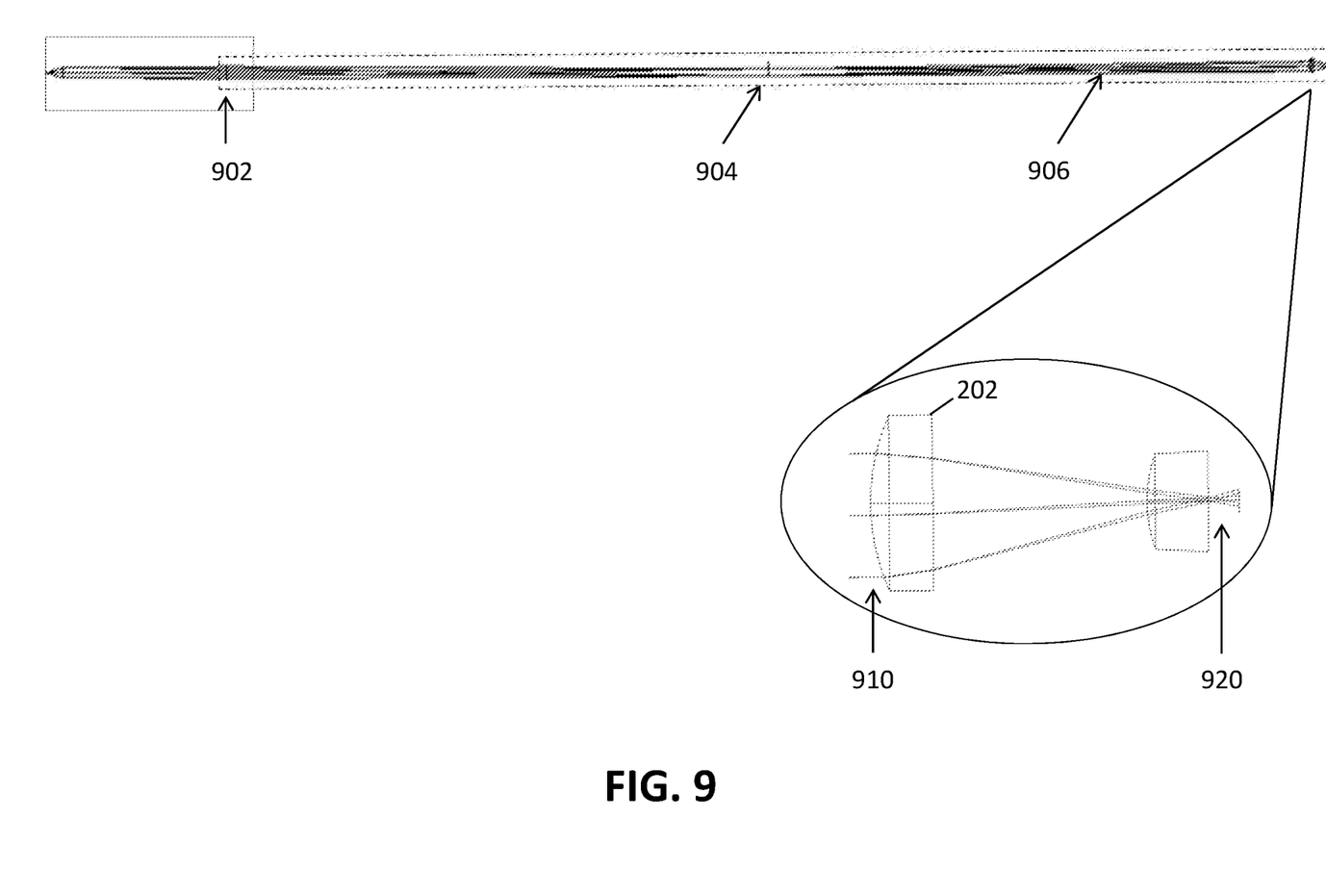
FIG. 9 illustrates how a design with two intermediate lenses in the end optic also desensitizes probe transmission to bending of the optic at the collet interface.

FIG. 9 further illustrates how a design with two intermediate lenses in the end optic desensitizes probe performance to bending of the optic at the collet interface. In FIG. 9, the tube may be tilted at the interface 902 by a small angle, as a nonlimiting example, 0.4°. As a result, the beam aperture is decentered on intermediate lens 904 due to the tube tilt. However, intermediate lens 904 functions to steer the beam back toward the longitudinal axis of the tube at point 906. The beam is now better centered at point 910 than it was on lens 904. As illustrated in the inset detail, although the image impinging on focus lens 202 is off-axis, this has a negligible effect on the position and quality of the sample focus 920.

Figure 10:
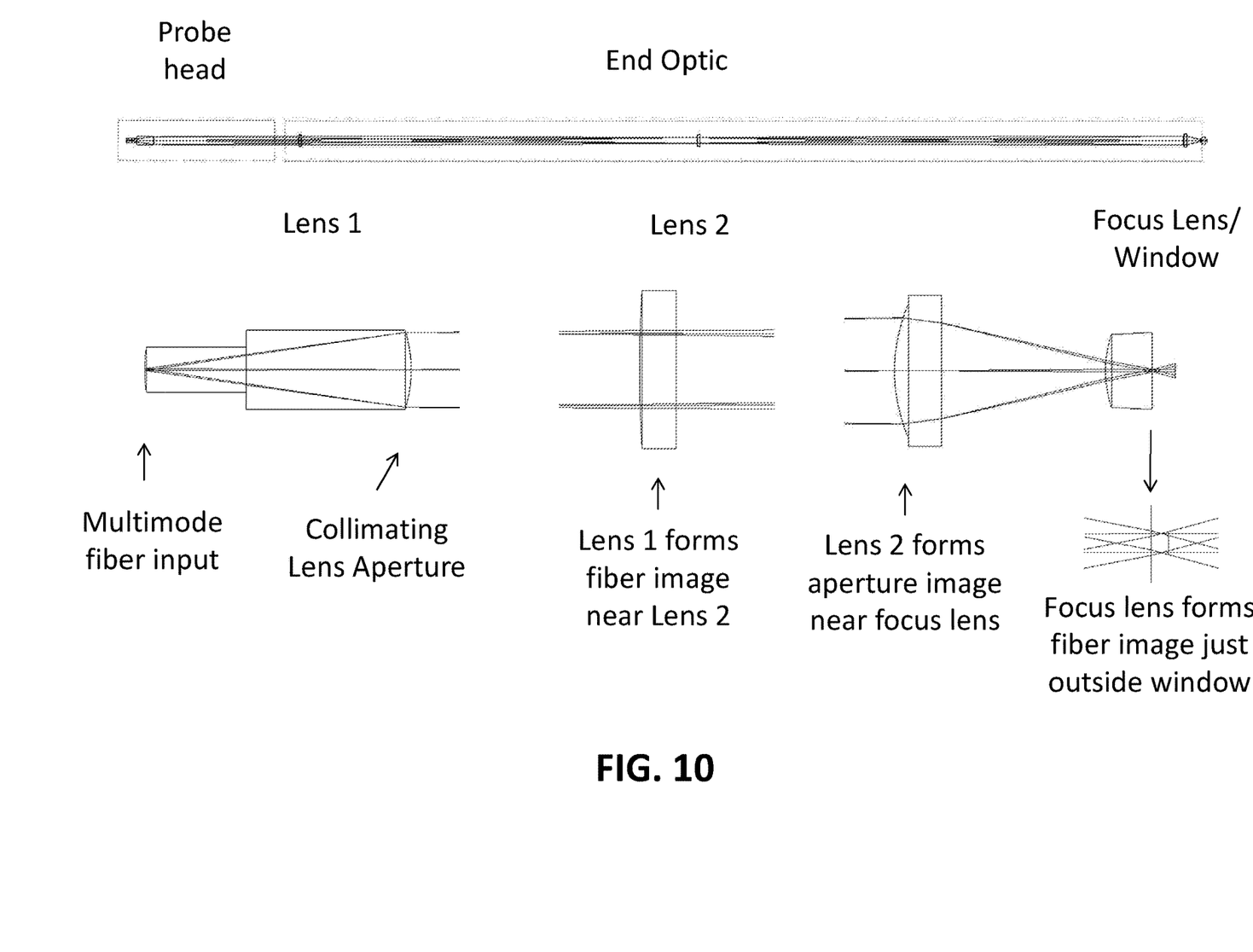
FIG. 10 illustrates an embodiment according to the present disclosure with two intermediate lenses in the end optic, and also shows details of the optical components used in the design.

By way of a review, FIG. 10 illustrates an embodiment with two intermediate lenses in the end optic and shows a drum lens used to collimate light from the multimode fiber input (as well as focus the sample collection to the fiber for delivery to a spectrograph, not shown). The use of a drum lens is inconsequential, and may be replaced with a more generic lens collimator in the probe head. As shown in FIG. 10, thin singlet lenses are used with optical materials selected for low background noise. However, in all embodiments, "lens" or "optics" should be taken to include doublets or groups of lenses intended to perform the designated functions disclosed herein.

While embodiments with first and second intermediate optics are disclosed and shown in the drawings, as end optic length (or length-to-aperture ratio) is further increased, the same design concepts can be extended to the addition of yet more intermediate lenses to relay aperture and fiber images across longer or smaller-diameter paths Again, it is stressed that the conventional rules of imaging endoscopes do not apply. With the present disclosure, excitation is delivered to, and light is collected from, a substantially homogeneous sample to characterize its constituents. The goal is maximum coupling of energy between the fiber(s) and the sample in both directions, with as high a numerical aperture as possible in the sample for maximum collection of excited spectra from the sample on the inbound path (e.g., Raman, fluorescence). Ideally, the entire fiber numerical aperture is focused at the sample point without vignetting the outbound laser power. Nevertheless, the focal spot can be an image of a fiber, the image of a lens aperture collimating a fiber, or a relay image of either. Such a relaxed requirement does not support a conventional multi-pixel imaging system, which must resolve different physical locations in the sample.

What is claimed is:

1. A spectroscopic probe, comprising:
    a probe head including an input fiber directed to a collimating lens having an aperture, the input fiber configured to convey an excitation beam and the collimating lens embodied to collimate and focus a single counter-propagating excitation-collection beam, the probe head further including an output fiber configured to convey a collection beam to a spectrograph; and
    an end optic comprising:
        an optical support structure having a proximal end and a distal end defining a length, wherein the proximal end of the optical support structure interfaces to the probe head such that the optical support structure carries the excitation-collection beam to and from a sample;
        an optical interface disposed at the distal end of the optical support structure, the optical interface including a focusing objective having an aperture for focusing the excitation-collection beam at one and only one focus point in the sample immediately adjacent to the optical interface; and
        one or more intermediate lenses supported between the collimating lens and the optical interface by the optical support structure, wherein the one or more intermediate lenses having a focal length selected to generate an image of the collimating lens aperture at the focusing objective, to match an exposure of the focusing objective aperture with the excitation-collection beam and reduce vignetting, and to maximize coupling of optical energy in both directions between the input and output fibers to and from the focus point in the sample.

2. The spectroscopic probe of claim 1, wherein the optical support structure is a hollow tube.

3. The spectroscopic probe of claim 1, wherein the optical support structure is a hollow tube, and the optical interface disposed at the distal end of the tube is a window sealed to the tube as to enable the end optic to be immersed within the sample, wherein the sample is a liquid.

4. The spectroscopic probe of claim 1, wherein the optical support structure is a hollow tube, and the optical interface disposed at the distal end of the tube is a cuvette or other sealed sample container.

5. The spectroscopic probe of claim 1, wherein the one or more intermediate lenses includes a first intermediate lens disposed at or near the proximal end of the optical support structure and a second intermediate lens disposed between the first intermediate lens and the focusing objective.

6. The spectroscopic probe of claim 5, wherein the first intermediate lens has a focal length selected to generate an image of the input fiber at or near the second intermediate lens, and wherein the second intermediate lens is operative to relay the collimating lens aperture to an image at or near the focusing objective.

7. The spectroscopic probe of claim 6, wherein the second intermediate lens is operative to generate an image of the collimating lens aperture at a point beyond the focusing objective to increase beam filling of the focusing objective aperture and improve the numerical aperture at the focus point in the sample.

8. The spectroscopic probe of claim 6, wherein the second intermediate lens is operative to steer the excitation-collection beam toward a center of the focusing objective in response to a bending of the optical support structure.

9. The spectroscopic probe of claim 1, wherein the input optical fiber is a multimode optical fiber.

10. The spectroscopic probe of claim 5, wherein the second intermediate lens is positioned in a region approximately midway along the length of the optical support structure.

\* \* \* \* \*